(12) United States Patent  
Cootsona (10) Patent No.: US 9,320,209 B2  
(45) Date of Patent: Apr. 26, 2016

(54) METHODS OF SORTING PLANT EMBRYOS

(71) Applicant: WEYERHAEUSER NR COMPANY, Federal Way, WA (US)

(72) Inventor: Craig N. Cootsona, Tacoma, WA (US)

(73) Assignee: WEYERHAEUSER NR COMPANY, Federal Way, WA (US)

( * ) Notice: Subject to any disclaimer, the term of this patent is extended or adjusted under 35 U.S.C. 154(b) by 358 days.

(21) Appl. No.: 14/134,029

(22) Filed: Dec. 19, 2013

(65) Prior Publication Data

US 2014/0186956 A1     Jul. 3, 2014

Related U.S. Application Data

(60) Provisional application No. 61/632,433, filed on Dec. 28, 2012.

(51) Int. Cl.
| | | |
|---|---|---|
| *C12N 5/00* | (2006.01) | |
| *C12N 5/02* | (2006.01) | |
| *C12N 5/04* | (2006.01) | |
| *A01C 1/06* | (2006.01) | |
| *A01H 4/00* | (2006.01) | |
| *C07K 14/415* | (2006.01) | |

(52) U.S. Cl.
CPC ............... *A01H 4/00* (2013.01); *A01H 4/005* (2013.01); *C07K 14/415* (2013.01)

(58) Field of Classification Search
CPC ........ A01H 4/005; C01K 14/415; A01C 1/06; A01C 1/04
USPC ........ 435/422, 430, 430.1, 419; 47/57.6, 1.01
See application file for complete search history.

(56) References Cited

U.S. PATENT DOCUMENTS

| | | | | |
|---|---|---|---|---|
| 8,931,208 B2 * | 1/2015 | Swanda | ................ | A01H 4/005 47/57.6 |
| 9,053,353 B2 * | 6/2015 | Timmis | .................... | A01C 1/00 |
| 2012/0202289 A1 | 8/2012 | Aidun | | |

* cited by examiner

*Primary Examiner* — Kent L Bell  
(74) *Attorney, Agent, or Firm* — Christensen O'Connor Johnson & Kindness PLLC (57) ABSTRACT

Methods of sorting plant somatic embryos according to germination potential are provided.

14 Claims, 7 Drawing Sheets

METHODS OF SORTING PLANT EMBRYOS

CROSS-REFERENCE TO RELATED APPLICATION

This application is entitled to and claims the benefit of priority under 35 U.S.C. §119 from U.S. Provisional Patent Application Ser. No. 61/632,433 filed Dec. 28, 2012, and titled "Methods of Sorting Plant Embryos," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as embryogenic suspensor masses, that are capable of developing into somatic embryos. The embryogenic tissue is then further cultured in a multiplication medium that promotes multiplication and mass production of the embryogenic tissue. The embryogenic tissue is then cultured in a development medium that promotes development and maturation of cotyledonary somatic embryos that may, for example, be placed on germination medium to produce germinants, and subsequently transferred to soil for further growth, or alternatively, placed within manufactured seeds and sown in soil where they germinate to yield seedlings. Manufactured seeds are described, for example, in U.S. Pat. Nos. 5,564,224; 5,687,504; 5,701,699; and 6,119,395.

The typical somatic embryogenesis process is laborious and inefficient. For example, one of the more labor intensive and subjective steps in the embryogenesis process is the selective harvesting of individual embryos suitable for germination. At the end of the development period, the embryos may be present in a number of stages of maturity and development. Those that are most likely to successfully germinate into normal plants are preferentially selected using a number of visually evaluated screening criteria. Typically, a skilled technician evaluates the morphological features of each embryo, such as the embryo's size, shape (e.g., axial symmetry), cotyledon development, surface texture, color, and the like, and manually plucks desirable embryos with a pair of tweezers and transfers the selected embryos to germination medium. The selection process is highly subjective, and the transferring of embryos to germination medium by hand remains a tedious, laborious, and ergonomically challenging process. Further, it poses a major production bottleneck when the ultimate desired output can be in the thousands of plants.

Efforts have been made to use instrumental image analysis for embryo selection to supplement or replace the visual evaluation performed by technicians. For example, an elaborate and complex classification method is disclosed in U.S. Publication No. 2007/0269096, which describes the classification of plant embryos by the application of classification algorithms to digitized images of plant embryos, and absorption, transmittance, or reflectance spectra of the embryos, to determine which embryos are likely to develop into germinants. Similarly, U.S. Pat. No. 7,610,155 describes using image and spectral data from known quality embryos to develop a classification model, using a classification algorithm, such as logistic regression (LR) analysis, to classify embryos as (i) embryos that likely will not germinate; (ii) embryos that may germinate with extra care; and (iii) embryos that will germinate with minimal care. The classification model is then applied to image and/or spectral data acquired from a plant embryo of unknown quality to determine the likelihood the embryo will develop into a germinant. Although determining the germination potential of embryos by classification modeling is a more objective process than selection of embryos by technicians, such methods involve the use of expensive instrumentation to collect the required images and data on each embryo, as well as extensive studies of embryos of known quality to develop the modeling system.

Thus, there exists a need for methods of selecting embryos that are most likely to successfully germinate into normal plants that simplify the process, reduce the need for selection by technician, and/or the use of expensive instrumentation, and increase the production rate to achieve commercial scale.

The present invention is directed to methods of sorting plant somatic embryos according to germination potential.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Methods of sorting plant somatic embryos according to germination potential are provided. Each of the methods includes the steps of: (a) placing a plurality of plant somatic embryos and fluid in a vessel; (b) stiffing the fluid and plant somatic embryos with sufficient speed to suspend the plant somatic embryos in the fluid and sort the plant somatic embryos according to germination potential; (c) dispensing the plant somatic embryos from the vessel in a fluid flow over a period of time, wherein the plant somatic embryos are dispensed over the period of time in order according to germination potential; and (d) depositing the plant somatic embryos on a substrate.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Unless specifically defined herein, all terms used herein have the same meaning as they would to one skilled in the art of the present disclosure.

As used herein, the term "embryogenic suspensor mass" (ESM) refers to early stage embryogenic cells in the process of multiplication by budding and cleavage.

As used herein, the term "plant embryo" refers to a somatic plant embryo. Somatic plant embryos may be produced by culturing embryogenic tissue by standard methods under laboratory conditions in which the cells comprising the tissue are separated from one another and induced to develop into minute complete embryos. As used herein, "plant embryo" includes embryos at various stages of development.

As used herein the term "germinant" refers to an immature plant that possesses a well developed radicle and cotyledonary structure with a growing epicotyl, both readily apparent to the naked eye, and ready for planting in soil. For example, germinants typically have an epicotyl of about 10 mm or greater.

As used herein, the terms "singulate" or "singulation" refers to the process of dispensing embryos on a substrate as individual, discrete embryos.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation or induction, to initiate formation of embryogenic tissue, such as an embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce embryogenic tissue; (3) development, to develop and form mature cotyledonary somatic embryos; and (4) post development steps such as separation, singulation, stratification, germination, placement into manufactured seeds, and transferring to soil for further growth and development.

At the end of the multiplication step, embryogenic tissue in the form of an embryogenic suspensor mass may be transferred to development medium for a period of time to develop into a plurality of cotyledonary embryos. At the end of the development period, the plurality of cotyledonary embryos are to various degrees attached to and embedded in suspensor tissue and residual underdeveloped ESM, together with incompletely developed embryos, abnormally formed embryos, undersized or oversized embryos, and other pieces of non-embryo plant material, and to other embryos. It is important for subsequent normal germination to separate each embryo from the suspensor mass and from other embryos to yield a plurality of individual embryos.

The plurality of individual embryos can be separated from ESM using aqueous liquid, such as water or an isotonic nutrient solution, to facilitate removal and washing away of any undesirable material, such as undersized embryos, tissues, and residual ESM. After the embryos have been separated from the ESM, the embryos can be further separated from each other into individual, discrete embryos, referred to herein as "singulation," to facilitate the selection of embryos that are most likely to successfully germinate into normal plants. Embryos can be singulated by mixing the embryos in a fluid in a vessel; dispensing the embryos and fluid from the vessel; and depositing the embryos on a substrate as individual discrete embryos.

The methods of the present disclosure are directed to sorting plant somatic embryos according to germination potential. The germination potential is related to the order in time in which the plant somatic embryos are dispensed from a vessel. Each of the methods includes the steps of: (a) placing a plurality of plant somatic embryos and fluid in a vessel; (b) stirring the fluid and plant somatic embryos with sufficient speed to suspend the plant somatic embryos in the fluid and sort the plant somatic embryos according to germination potential; (c) dispensing the plant somatic embryos from the vessel in a fluid flow over a period of time, wherein the plant somatic embryos are dispensed over the period of time in order according to germination potential; and (d) depositing the plant somatic embryos on a substrate. In some embodiments, the plant somatic embryos dispensed later in the period of time have a germination potential that is greater than the germination potential of the plant somatic embryos dispensed earlier in the period of time.

In some embodiments, the fluid and plant somatic embryos are stirred in a vortex arrangement. While not being bound by any specific theory, the vortex arrangement may sort the plant somatic embryos according to physical characteristics, e.g., density, shape, buoyancy, and/or surface tension or other physical characteristic, which are related to germination potential.

In some embodiments, the plant somatic embryos are dispensed from the vessel over a period of time of from less than about ten minutes to about sixty-five minutes. In some embodiments the period of time is from about 5 minutes to about ten minutes. In some embodiments the period of time is about thirty minutes. In some embodiments the period of time is about sixty minutes.

Plant somatic embryos suitable for use in the methods of the invention may be from any plant species, such as dicotyledonous or monocotyledonous plants, gymnosperms, etc. Conifer embryos are suitable for use in the methods of the invention and may be from any conifer species including, but not limited to, species within the genera *Pinus, Picea, Tsuga, Pseudotsuga, Thuja, Juniperis, Larix*, and *Sequoia*.

In some embodiments, the plurality of plant somatic embryos are conifer somatic embryos. In some embodiments, the plurality of conifer somatic embryos are somatic embryos of the family Pinaceae. In some embodiments, the plurality of conifer somatic embryos are loblolly-pine somatic embryos. In some embodiments, the plurality of conifer somatic embryos are Douglas-fir somatic embryos.

In some embodiments, the methods of the present disclosure further include the steps of transferring the plurality of plant somatic embryos to germination medium and culturing the plant somatic embryos to form germinants.

EXAMPLES

The following example are provided for the purpose of illustrating, not limiting, the present disclosure.

Example 1

Figure 1:
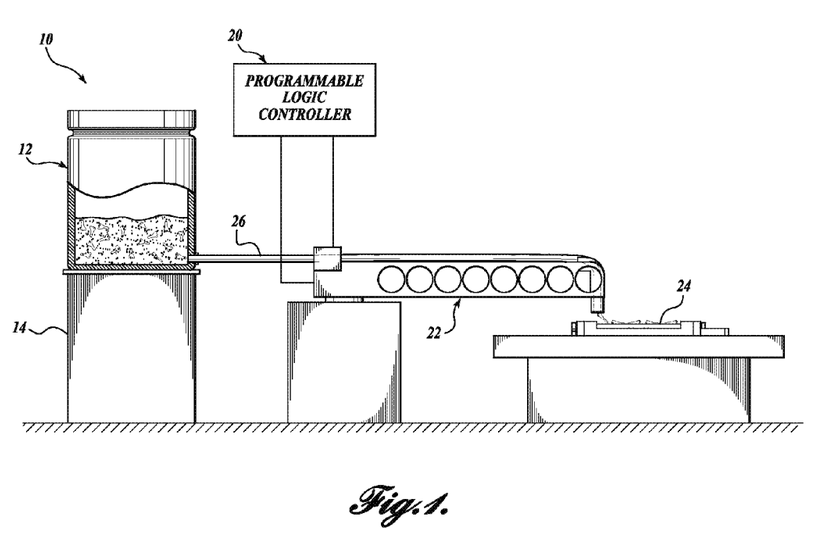
FIG. 1 is a schematic illustration of a system that can be used in practicing the methods of the present disclosure.

This example describes an exemplary system that can be used in the methods of the present disclosure, which is illustrated in FIG. 1. Referring to FIG. 1, the system includes an embryo dispensing assembly 10, a programmable logic controller (PLC) 20, a mechanism 22, which is used to deposit individual embryos on a substrate 24, and an embryo dispensing tubing 26. The embryo dispensing assembly 10 includes a vessel 12 and a stir plate 14. An embryo dispensing tubing 26 extends from the vessel 12 to the mechanism 22.

During operation, embryos are received at the embryo dispensing assembly 10 and deposited in the vessel 12. A suitable fluid, e.g. ultrapure water, is also supplied to the vessel 12.

The vessel 12 is in communication with a stir plate 14 to stir the fluid in the vessel 12 to a sufficient degree to maintain the embryos in suspension in a vortex arrangement in the fluid. The stir plate 14 is in communication with the PLC 20 to automatically adjust the amount of stirring that occurs. The PLC 20 is programmed so that the stirring speed linearly, or at another rate, decreases as the fluid level in the vessel 12 decreases as embryos are dispensed from the vessel 12 through the embryo dispensing tubing 26.

The embryo dispensing tube 26 extends between the vessel 12 and the mechanism 22. Embryos are transported from the vessel 12 to the mechanism 22 by fluid flowing through the embryo dispensing tubing 26. The rate of fluid flowing through the tubing 26 can be about 250-550 ml/minute. The flow rate of embryos through the tubing 26 can be at a rate of about 250-450 embryos/minute. The embryos exit the mechanism 22 and are deposited on a substrate 24. The substrate 24 can be mounted in a frame.

Example 2

In this example, the germination potential of somatic embryos was observed as a function of the order in time in which the embryos were dispensed from a vessel and deposited on a substrate.

Using an embodiment of the system described in FIG. 1, loblolly pine embryos were suspended in about 6.5 liters of water in a vessel and stirred at 22 Hz. Fluid was dispensed from the vessel at the rate of about 250-300 mL/minute. The embryos were dispensed from the vessel at a rate of about 250-450 embryos/minute and deposited on a number of substrates mounted in frames over a period of time. Three time periods were studied, as shown in Table 1.

TABLE 1

| Time Period | Frame | Overall Frame Order | Kettle Volume mL | Stir Speed (Hz) | Kettle Stir/Mix Time |
|---|---|---|---|---|---|
| 1 | 1 | 1 | 6500 | 22 | 0:04:52 |
| 1 | 2 | 2 | 6186 | 22 | 0:05:56 |
| 1 | 3 | 3 | 5858 | 22 | 0:06:57 |
| 1 | 4 | 4 | 5559 | 22 | 0:08:10 |
| 1 | 5 | 5 | 5238 | 22 | 0:09:06 |
| 1 | 6 | 6 | 4963 | 22 | 0:10:03 |
| 2 | 1 | 7 | 6307 | 22 | 0:25:40 |
| 2 | 2 | 8 | 5954 | 22 | 0:26:50 |
| 2 | 3 | 9 | 5500 | 22 | 0:27:55 |
| 2 | 4 | 10 | 5290 | 22 | 0:28:52 |
| 2 | 5 | 11 | 5018 | 22 | 0:29:50 |
| 2 | 6 | 12 | 4757 | 22 | 0:31:38 |
| 3 | 1 | 13 | 6232 | 22 | 0:55:43 |
| 3 | 2 | 14 | 5934 | 22 | 0:56:40 |
| 3 | 3 | 15 | 5630 | 22 | 0:57:45 |
| 3 | 4 | 16 | 5333 | 22 | 0:58:47 |
| 3 | 5 | 17 | 5050 | 22 | 0:59:59 |
| 3 | 6 | 18 | 4766 | 22 | 1:01:01 |

Bold numbers denote water refills

For Time Period 1, the embryos were dispensed from the vessel over a period of time beginning at about 5 minutes and continuing for an additional 5 minutes. For Time Period 2, the embryos were dispensed from the vessel over a period of time beginning at about 25 minutes and continuing for an additional 5 minutes. For Time Period 3, the embryos were dispensed from the vessel over a period of time beginning at about 55 minutes and continuing for an additional 5 minutes. The embryos were deposited on the substrates ("frames") at a density of about 200-400 embryos per substrate. The embryos were conditioned over water and then transferred en masse to germination medium. No efforts were made to select embryos based on any criteria. The embryos were cultured over a period of time sufficient to produce germinants.

Results

The germinants were scored according to certain criteria: Category 1, bipolar and an epicotyl of about 5 mm; Category 2, bipolar; Category 3, root only; Category 4, epicotyl only; and Category 5, dead or unchanged. Data analysis was performed as follows: proportion responses were modeled using a generalized linear mixed model with the binomial distribution and logit link. The log transformation was used to obtain homogenous variance. Means and confidence intervals were transformed back to the natural scale.

The results are shown in Tables 2 and 3 and FIGS. 2-7.

It was found that the mean percent of total dispensed embryos that developed into Category 1 germinants (represented herein by "P-1") increased linearly overtime; i.e. P-1 at Time Period 1<P-1 at Time Period 2<P-1 at Time Period 3 (data not shown).

The data in Table 2 summarizes test results comparing combined means for Category 1 germinants

TABLE 2

Germination (Category 1) comparison of estimated means

| Time Period | Test at $\alpha = 0.10$ |
|---|---|
| 1 | C |
| 2 | B |
| 3 | A |

The column "Test at $\alpha=0.10$" summarizes test results comparing combined means. Means with different symbols are statistically different at $\alpha=0.10$.

Figure 2:
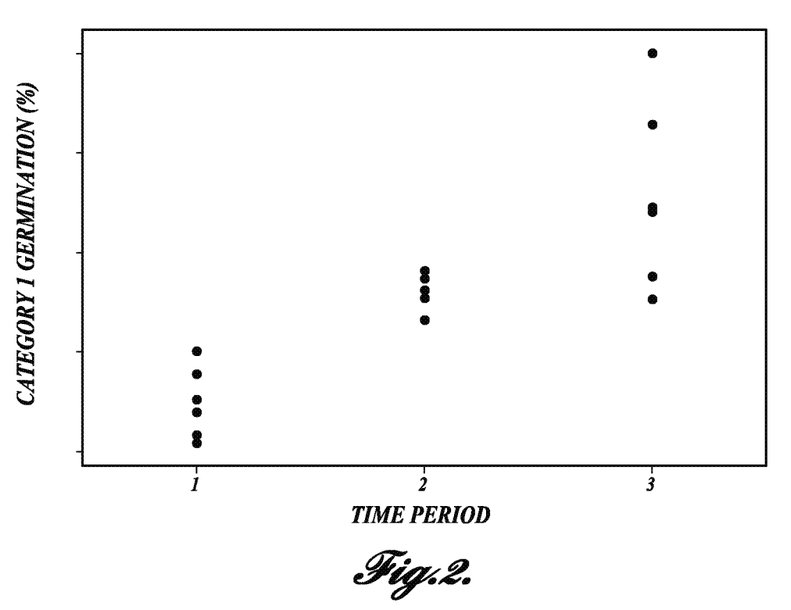
FIG. 2 is a graph showing the relative percents, at specific time points, of total dispensed embryos that developed into Category 1 germinants.
Figure 3:
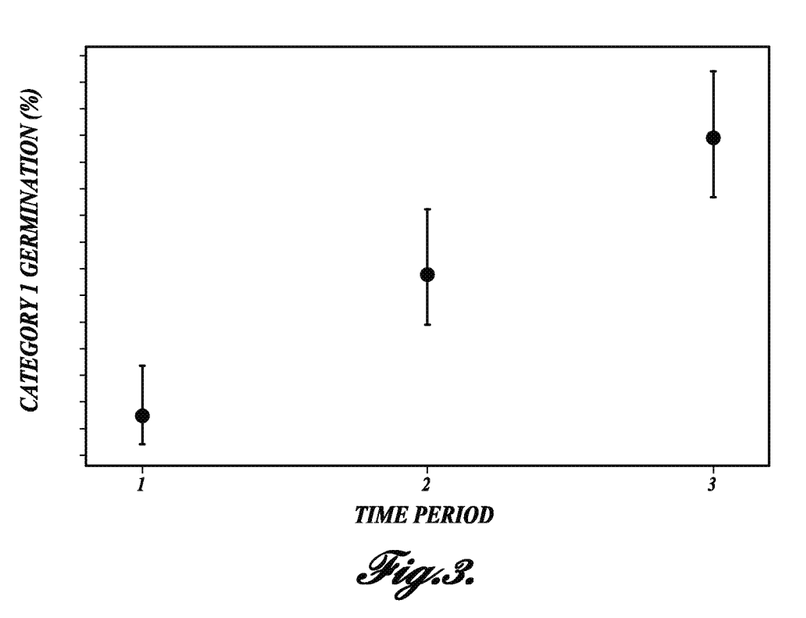
FIG. 3 is a graph showing the relative least means square percents, at specific time points, of total dispensed embryos that developed into Category 1 germinants.

As shown in Table 2, the differences in mean percent of total dispensed embryos that developed into Category 1 germinants at each time period was statistically significant. The relative percents and relative least square means percents are also shown in FIGS. 2 and 3, respectively. Referring to FIG. 3, the error bars represent 90% confidence limits.

Figure 4:
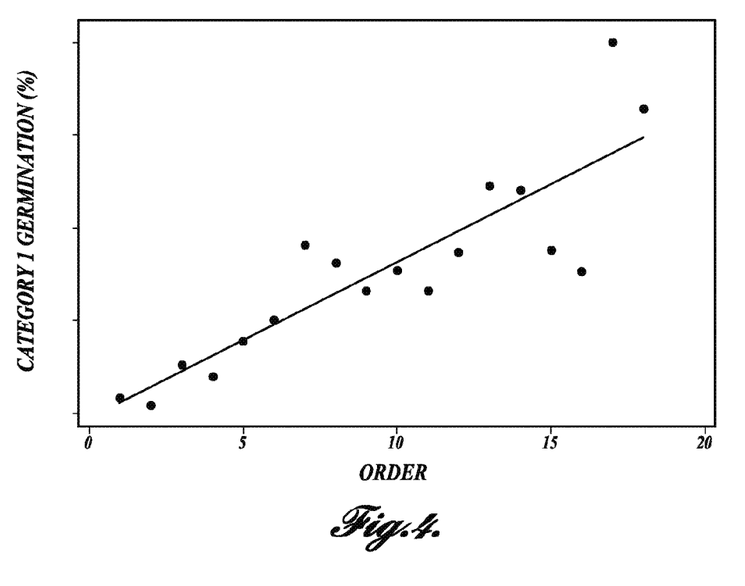
FIG. 4 is a graph showing the relative percents over time of total dispensed embryos that developed into Category 1 germinants.

FIG. 4 is a graph showing the relative percents over time of total dispensed embryos that developed into Category 1 germinants. It can be seen in FIG. 4 that the percent of total dispensed embryos that developed into Category 1 germinants increased linearly over time.

The percent of embryos that developed into Category 1 germinants as a function of the order in time in which the embryos were dispensed from a vessel and deposited on a substrate was found to be statistically significant (p value=0.0003).

It was also found that the mean percent of total dispensed embryos that developed into Category 1+2 germinants (represented herein by "P-1+2") increased overtime; i.e. P-1+2 at Time Period 1<P-1+2 at Time Period 2<P-1+2 at Time Period 3 (data not shown).

The data in Table 3 summarizes test results comparing combined means for Category 1+2 germinants.

TABLE 3

Germination (Category 1 + 2) estimated means and comparisons

| Time Period | Test at $\alpha = 0.10$ |
|---|---|
| 1 | C |
| 2 | B |
| 3 | A |

The column "Test at $\alpha=0.10$" summarizes test results comparing combined means. Means with different symbols are statistically different at $\alpha=0.10$.

Figure 5:
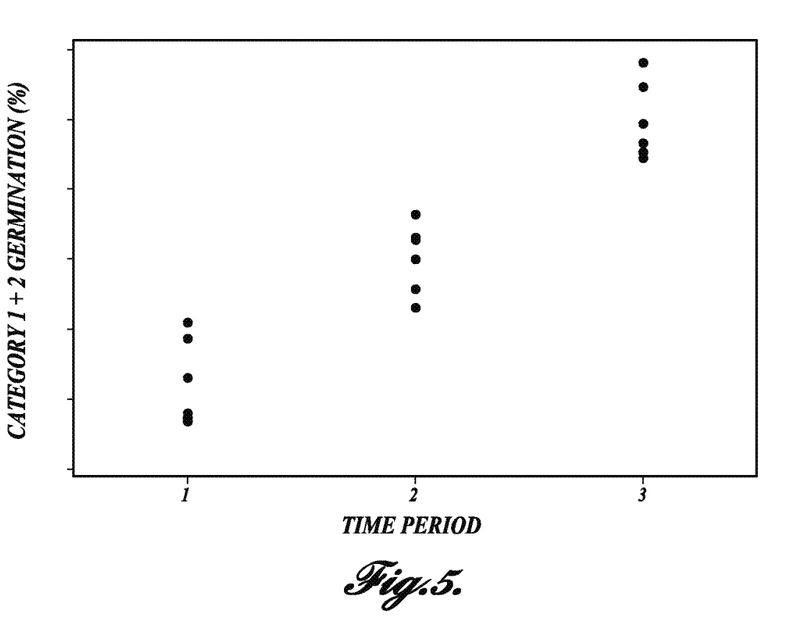
FIG. 5 is a graph showing the relative percents, at specific time points, of total dispensed embryos that developed into Category 1+2 germinants.
Figure 6:
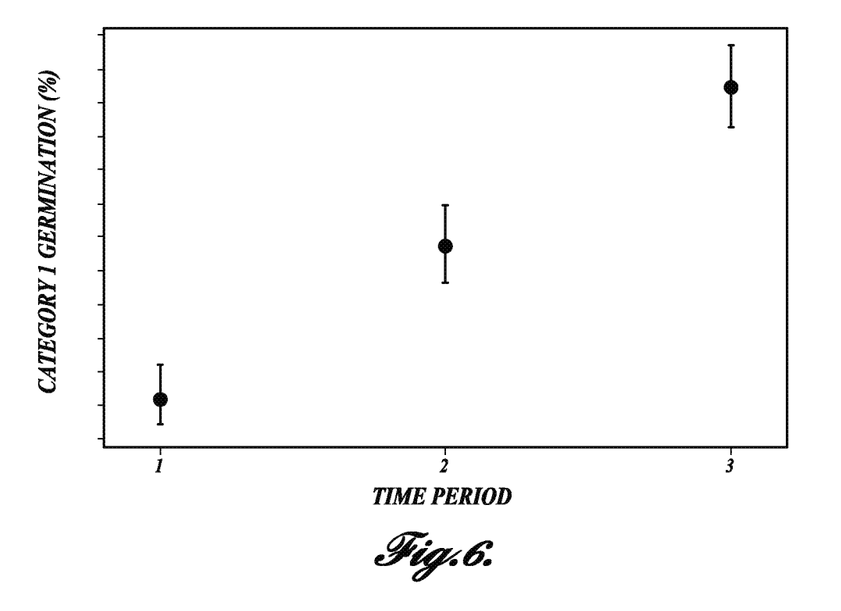
FIG. 6 is a graph showing the relative least means square percents, at specific time points, of total dispensed embryos that developed into Category 1+2 germinants.

As shown in Table 3, the differences in mean percent of total dispensed embryos that developed into Category 1+2 germinants at each time period was statistically significant. The relative percents and relative least square means percents are also shown in FIGS. 5 and 6, respectively. Referring to FIG. 6, the error bars represent 90% confidence limits.

Figure 7:
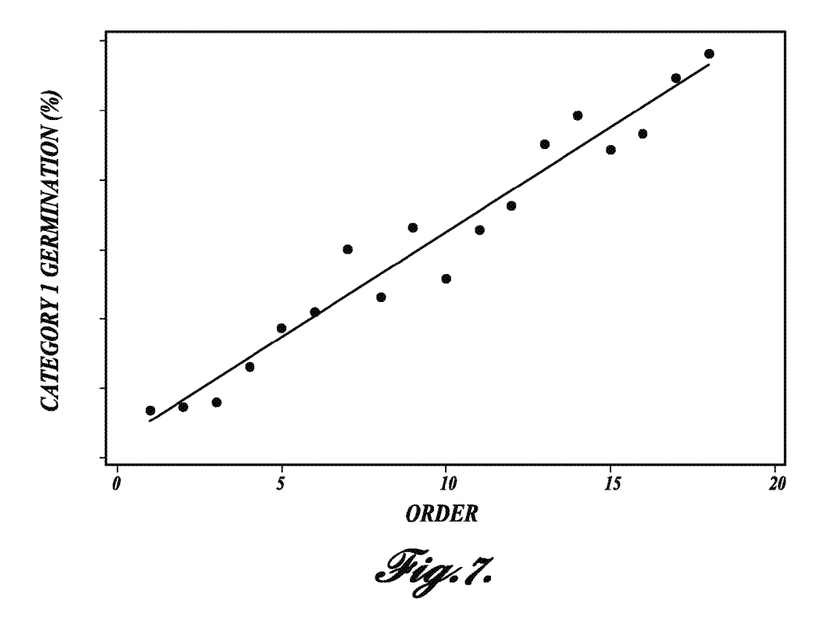
FIG. 7 is a graph showing the relative percents over time of total dispensed embryos that developed into Category 1+2 germinants.

FIG. 7 is a graph showing the relative percents over time of total dispensed embryos that developed into Category 1+2 germinants. It can be seen in FIG. 7 that the percent of total dispensed embryos that developed into Category 1+2 germinants increased linearly over time.

The percent of embryos that developed into Category 1+2 germinants as a function of the order in time in which the embryos were dispensed from a vessel and deposited on a substrate was found to be statistically significant (p value<0.0001).

In this Example 2, embryos were dispensed from the vessel over time periods of up to about one hour. It is expected that the percent of embryos dispensed over times greater than one hour that develop into Category 1 or Category 1+2 germinants could be even higher than the percent of embryos dispensed earlier in time that develop into Category 1 or Category 1+2 germinants. It is also expected that the linear nature of the increase would continue for time periods greater than one hour.

The results described above were surprising. It was thought that the stirring process itself, and/or the length of time the embryos spent in the fluid in the vessel, would have an adverse impact on the embryos and ultimately on germination. Therefore, it was expected that embryos dispensed earlier in time would have a higher germination potential than embryos dispensed later in time. However, it was unexpectedly discovered that embryos dispensed later in time had a higher germination potential than embryos dispensed earlier in time and the increase in germination potential was linear as a function of time.

While illustrative embodiments have been illustrated and described, it will be appreciated that various changes can be made therein without departing from the spirit and scope of the invention.

The invention claimed is:

1. A method of sorting plant somatic embryos according to germination potential comprising the steps of:
   (a) placing a plurality of plant somatic embryos and fluid in a vessel;
   (b) stirring the fluid and plant somatic embryos with sufficient speed to suspend the plant somatic embryos in the fluid and sort the plant somatic embryos according to germination potential;
   (c) dispensing the plant somatic embryos from the vessel in a fluid flow over a period of time, wherein the plant somatic embryos are dispensed over the period of time in order according to germination potential; and
   (d) depositing the plant somatic embryos on a substrate.

2. The method of claim 1, wherein the plant somatic embryos dispensed later in the period of time have a germination potential that is greater than the germination potential of plant somatic embryos dispensed earlier in the period of time.

3. The method of claim 1, wherein the fluid and plant somatic embryos are stirred in a vortex arrangement.

4. The method of claim 1, wherein the period of time is from about less than ten minutes to about sixty-five minutes.

5. The method of claim 4, wherein the period of time is from about 5 minutes to about ten minutes.

6. The method of claim 4, wherein the period of time is about thirty minutes.

7. The method of claim 4, wherein the period of time is about sixty minutes.

8. The method of claim 1, wherein the plant somatic embryos are dispensed from the vessel at a fluid flow rate of about 250-450 embryos/minute.

9. The method of claim 1, wherein the plurality of plant somatic embryos are conifer somatic embryos.

10. The method of claim 9, wherein the plurality of conifer somatic embryos are somatic embryos of the family Pinaceae.

11. The method of claim 10, wherein the plurality of conifer somatic embryos are loblolly-pine somatic embryos.

12. The method of claim 10, wherein the plurality of conifer somatic embryos are Douglas-fir somatic embryos.

13. The method of claim 1, further comprising the step of transferring the plurality of plant somatic embryos to germination medium.

14. The method of claim 13, further comprising culturing the plant somatic embryos on germination medium to form germinants.

* * * * *